(12) United States Patent
Olesen et al.

(10) Patent No.: US 12,383,676 B2
(45) Date of Patent: *Aug. 12, 2025

(54) AUTO INJECTOR WITH CHARGER SAFETY

(71) Applicant: Ascendis Pharma A/S, Hellerup (DK)

(72) Inventors: Jan Olesen, Holstebro (DK);
Flemming Madsen, Aalborg (DK)

(73) Assignee: Ascendis Pharma A/S, Hellerup (DK)

( * ) Notice: Subject to any disclaimer, the term of this patent is extended or adjusted under 35 U.S.C. 154(b) by 0 days.

This patent is subject to a terminal disclaimer.

(21) Appl. No.: 18/346,693

(22) Filed: Jul. 3, 2023

(65) Prior Publication Data

US 2023/0338659 A1    Oct. 26, 2023

Related U.S. Application Data

(63) Continuation of application No. 17/829,161, filed on May 31, 2022, now Pat. No. 11,738,147, which is a (Continued)

(30) Foreign Application Priority Data

Dec. 30, 2015    (EP) .................................. 15203173

(51) Int. Cl.
*A61M 5/20*    (2006.01)
*A61M 5/24*    (2006.01)
*A61M 5/32*    (2006.01)

(52) U.S. Cl.
CPC ............... *A61M 5/20* (2013.01); *A61M 5/24* (2013.01); *A61M 5/3202* (2013.01); (Continued)

(58) Field of Classification Search
CPC ........ A61M 5/20; A61M 5/24; A61M 5/3202; A61M 2005/2411; A61M 2205/50; (Continued)

(56) References Cited

U.S. PATENT DOCUMENTS

| | | |
|---|---|---|
| 4,024,864 A | 5/1977 | Davies |
| 4,394,863 A | 7/1983 | Bartner |

(Continued)

FOREIGN PATENT DOCUMENTS

| | | |
|---|---|---|
| CN | 101905048 | 12/2010 |
| CN | 102413855 | 4/2012 |

(Continued)

OTHER PUBLICATIONS

US 11,957,880 B2, 04/2024, Jensen et al. (withdrawn)

(Continued)

*Primary Examiner* — Dung T Ulsh
(74) *Attorney, Agent, or Firm* — Knobbe, Martens, Olson & Bear, LLP

(57) ABSTRACT

An auto injector is disclosed comprising: a housing, a cartridge receiver, and an ejector member. The cartridge receiver is configured to receive a cartridge containing the medicament. The auto injector further comprises a blocking member coupled to an ejector member. The blocking member is configured to move between a blocking position wherein a connector opening is blocked and a non-blocking position wherein the connector opening is not blocked.

15 Claims, 9 Drawing Sheets

Related U.S. Application Data continuation of application No. 16/060,608, filed as application No. PCT/EP2016/082861 on Dec. 29, 2016, now Pat. No. 11,406,760.

(52) U.S. Cl.
CPC . *A61M 2005/2411* (2013.01); *A61M 2205/50* (2013.01); *A61M 2205/502* (2013.01); *A61M 2205/82* (2013.01); *A61M 2205/8206* (2013.01); *A61M 2205/8237* (2013.01); *A61M 2205/8262* (2013.01)

(58) Field of Classification Search
CPC .. A61M 2205/8206; A61M 2205/8237; A61M 2205/8262
See application file for complete search history.

(56) References Cited

U.S. PATENT DOCUMENTS

| | | |
|---|---|---|
| 4,677,980 A | 7/1987 | Reilly et al. |
| 5,739,508 A | 4/1998 | Uber, III |
| 5,808,203 A | 9/1998 | Nolan, Jr. et al. |
| 6,368,314 B1 | 4/2002 | Kipfer et al. |
| 9,173,995 B1 | 11/2015 | Tucker |
| 10,384,031 B1 | 8/2019 | Acker et al. |
| 10,835,677 B2 | 11/2020 | Fabricius et al. |
| 11,179,524 B2 | 11/2021 | Pedersen et al. |
| 11,351,305 B2 | 6/2022 | Pedersen et al. |
| 11,406,760 B2 | 8/2022 | Olesen et al. |
| 11,517,673 B2 | 12/2022 | Pedersen et al. |
| 11,524,115 B2 | 12/2022 | Jacobsen et al. |
| 11,607,496 B2 | 3/2023 | Fabricius et al. |
| 11,684,724 B2 | 6/2023 | Egesborg et al. |
| 11,738,147 B2 | 8/2023 | Olesen et al. |
| 11,969,581 B2 | 4/2024 | Pedersen et al. |
| 12,005,241 B2 | 6/2024 | Pedersen et al. |
| 2002/0016573 A1 | 2/2002 | Munk |
| 2002/0107477 A1 | 8/2002 | Kipfer |
| 2003/0083626 A1 | 5/2003 | Munk et al. |
| 2003/0205587 A1 | 11/2003 | Tribe |
| 2005/0261634 A1 | 11/2005 | Karlsson |
| 2006/0178630 A1 | 8/2006 | Bostrom et al. |
| 2009/0036846 A1 | 2/2009 | Dacquay et al. |
| 2009/0209883 A1 | 8/2009 | Higgins et al. |
| 2009/0299328 A1 | 12/2009 | Mudd et al. |
| 2010/0069842 A1 | 3/2010 | Dos Santos et al. |
| 2010/0094309 A1 | 4/2010 | Boukhny et al. |
| 2010/0211005 A1 | 8/2010 | Edwards et al. |
| 2011/0313395 A1 | 12/2011 | Krulevitch et al. |
| 2012/0078185 A1 | 3/2012 | Smith et al. |
| 2012/0204997 A1 | 8/2012 | Winn et al. |
| 2012/0283655 A1 | 11/2012 | Plumptre et al. |
| 2013/0079708 A1 | 3/2013 | Wiimpenny et al. |
| 2013/0193073 A1 | 8/2013 | Hogard et al. |
| 2013/0211326 A1 | 8/2013 | Dasbach et al. |
| 2013/0211327 A1 | 8/2013 | Osman et al. |
| 2013/0226134 A1 | 8/2013 | Schabbach et al. |
| 2013/0245545 A1 | 9/2013 | Arnold et al. |
| 2013/0281965 A1 | 10/2013 | Kamen et al. |
| 2013/0296807 A1 | 11/2013 | Lintern et al. |
| 2014/0012229 A1 | 1/2014 | Bokelman et al. |
| 2014/0114277 A1 | 4/2014 | Eggert et al. |
| 2014/0142514 A1 | 5/2014 | Elahi et al. |
| 2014/0166915 A1 | 6/2014 | Ishibashi et al. |
| 2014/0188076 A1 | 7/2014 | Kamen et al. |
| 2014/0193788 A1 | 7/2014 | Groves et al. |
| 2014/0207106 A1 | 7/2014 | Bechmann et al. |
| 2014/0221925 A1 | 8/2014 | Kondoh et al. |
| 2014/0358093 A1 | 12/2014 | Soerensen et al. |
| 2015/0045729 A1 | 2/2015 | Denzer et al. |
| 2015/0051538 A1 | 2/2015 | Hata et al. |
| 2015/0088089 A1 | 3/2015 | Bartlett et al. |
| 2015/0122338 A1 | 5/2015 | Hunter et al. |
| 2015/0231334 A1 | 8/2015 | Buchine et al. |
| 2015/0306316 A1 | 10/2015 | Bruggemann |
| 2015/0320932 A1* | 11/2015 | Draper ................ A61M 5/1454 604/131 |
| 2015/0359967 A1* | 12/2015 | Steel ..................... A61M 5/345 604/192 |
| 2015/0367074 A1* | 12/2015 | Draper ................... A61M 5/20 604/198 |
| 2015/0367075 A1 | 12/2015 | Cave |
| 2015/0374930 A1 | 12/2015 | Hyde et al. |
| 2017/0119969 A1 | 5/2017 | McCullough et al. |
| 2017/0196702 A1 | 7/2017 | Agarwal |
| 2018/0094309 A1 | 4/2018 | Boukhany |
| 2018/0236181 A1 | 8/2018 | Marlin et al. |
| 2022/0152310 A1 | 5/2022 | Pedersen et al. |
| 2022/0288316 A1 | 9/2022 | Olesen et al. |
| 2023/0016657 A1 | 1/2023 | Pedersen et al. |
| 2023/0072178 A1 | 3/2023 | Jacobsen et al. |
| 2023/0090661 A1 | 3/2023 | Jensen et al. |
| 2023/0263961 A1 | 8/2023 | Egesborg et al. |
| 2023/0270945 A1 | 8/2023 | Fabricius et al. |
| 2024/0082494 A1 | 3/2024 | Jensen et al. |
| 2024/0165336 A1 | 5/2024 | Pedersen et al. |
| 2024/0277944 A1 | 8/2024 | Pedersen et al. |
| 2024/0374827 A1 | 11/2024 | Egesborg et al. |

FOREIGN PATENT DOCUMENTS

| | | |
|---|---|---|
| CN | 102740907 | 10/2012 |
| CN | 103813820 | 5/2014 |
| CN | 105492047 | 4/2016 |
| EP | 2656865 | 10/2013 |
| EP | 2675500 | 12/2013 |
| EP | 2777731 | 9/2014 |
| EP | 2923715 | 9/2015 |
| GB | 2356349 | 5/2001 |
| GB | 2506918 | 4/2014 |
| JP | H11513586 | 11/1999 |
| JP | 2000-513973 | 10/2000 |
| JP | 2005-503202 | 2/2005 |
| JP | 2005-080832 | 3/2005 |
| JP | 2007-500531 | 1/2007 |
| JP | 2008-531235 | 8/2008 |
| JP | 2009-148591 | 7/2009 |
| JP | 2009-279438 | 12/2009 |
| JP | 2010-506681 | 3/2010 |
| JP | 2010-510011 | 4/2010 |
| JP | 2010-523181 | 7/2010 |
| JP | 2011-507668 | 3/2011 |
| JP | 2011-521744 | 7/2011 |
| JP | 2011-240159 | 12/2011 |
| JP | 2012-505066 | 3/2012 |
| JP | 2012-066767 | 4/2012 |
| JP | 2012-516737 | 7/2012 |
| JP | 2012-519028 A | 8/2012 |
| JP | 2013-506444 | 2/2013 |
| JP | 2013-069305 | 4/2013 |
| JP | 2013-075154 | 4/2013 |
| JP | 2013-537844 | 10/2013 |
| JP | 2014-500746 | 1/2014 |
| JP | 2014-502890 | 2/2014 |
| JP | 2014-503279 | 2/2014 |
| JP | 2014-506159 | 3/2014 |
| JP | 2014-507223 | 3/2014 |
| JP | 2014-515941 | 7/2014 |
| JP | 2014-516700 | 7/2014 |
| JP | 2014-516702 | 7/2014 |
| JP | 2014-521113 | 8/2014 |
| JP | 2014-4528787 | 10/2014 |
| JP | 2015-521920 | 8/2015 |
| JP | 2015-163208 | 9/2015 |
| JP | 2016-208611 | 12/2016 |
| JP | 2001-513371 | 9/2021 |
| KR | 10-2015-0125701 | 11/2015 |
| KR | B-10-1666755 | 10/2016 |
| KR | 10-2017-0013870 | 2/2017 |
| PT | 3397321 | 10/2022 |
| RU | 2014-120469 | 11/2015 |
| WO | WO 2002/051471 | 7/2002 |
| WO | WO 2005/102416 | 11/2005 |

(56) References Cited

FOREIGN PATENT DOCUMENTS

| | | |
|---|---|---|
| WO | WO 2006/116997 | 11/2006 |
| WO | WO 2008/062025 | 5/2008 |
| WO | WO 2006/059597 | 6/2008 |
| WO | WO 2010/098927 | 9/2010 |
| WO | WO 2010/098931 | 9/2010 |
| WO | WO 2012/112347 | 8/2012 |
| WO | WO 2010/100883 | 9/2012 |
| WO | WO 2012/160157 | 11/2012 |
| WO | WO 2013/065055 | 5/2013 |
| WO | WO 2013/138830 | 9/2013 |
| WO | WO 2014/008393 | 1/2014 |
| WO | WO 2012/066767 | 5/2014 |
| WO | WO 2014/118106 | 8/2014 |
| WO | WO 2014/118109 | 8/2014 |
| WO | WO 2014/118110 | 8/2014 |
| WO | WO 2014/144096 | 9/2014 |
| WO | WO 2014/166915 | 10/2014 |
| WO | WO 2014/168205 | 10/2014 |
| WO | WO 2014/187812 | 11/2014 |
| WO | WO 2014/187813 | 11/2014 |
| WO | WO 2015/006430 | 1/2015 |
| WO | WO 2013/069305 | 4/2015 |
| WO | WO 2015/055640 | 4/2015 |
| WO | WO 2015/055642 | 4/2015 |
| WO | WO 2015/115326 | 8/2015 |
| WO | WO 2015/187797 | 12/2015 |
| WO | WO 2016/005421 | 1/2016 |
| WO | WO 2016/033507 | 3/2016 |
| WO | WO 2016/098060 | 6/2016 |
| WO | WO 2014/091765 | 1/2017 |
| WO | WO 2017/009724 | 1/2017 |
| WO | WO 2017/114906 | 7/2017 |
| WO | WO 2017/114907 | 7/2017 |
| WO | WO 2017/114908 | 7/2017 |
| WO | WO 2017/114909 | 7/2017 |
| WO | WO 2017/114910 | 7/2017 |
| WO | WO 2017/114911 | 7/2017 |
| WO | WO 2017/114912 | 7/2017 |
| WO | WO 2018/215516 | 11/2018 |
| WO | WO 2019/002534 | 1/2019 |
| WO | WO 2020/176319 | 9/2020 |
| WO | WO 2023/052487 | 4/2023 |

OTHER PUBLICATIONS

English Translation of Office Action dated Jun. 3, 2021, in Corresponding Chinese Application No. 201880043795.0.
English Translation of Office Action dated Jul. 9, 2021, in corresponding Russian Application No. 2019140269.
English Translation of Office Action dated Jul. 30, 2021, in corresponding Russian Application No. 2020103216.
English Translation of Office Action dated Jun. 10, 2021, in corresponding Chinese Application No. 201880033657.4.
English translation of Office Action issued in Japanese Application No. 2019-565323, dated Jan. 5, 2022.
English translation of Office Action issued in Japanese Application No. 2019-570894, dated Jan. 13, 2022.
English translation of Office Action issued in Chinese Application No. 201880033657, dated Feb. 23, 2022.
English translation of Office Action issued in Japanese Application No. 2021-116315, dated Sep. 2, 2022.
English translation of Office Action issued in Korean Application No. 10-2020-7000564, dated Oct. 17, 2022.
European Search Report for EP 15203132.4, dated Jun. 29, 2016.
European Search Report for EP 15203137.3, dated Jul. 1, 2016.
Partial European Search Report for EP15203168.8, dated Sep. 16, 2016.
European Search Report for EP 18733296.0, dated Feb. 1, 2023, in 5 pages.
International Search Report for PCT/EP2016/082861, dated Mar. 22, 2017.
International Preliminary Report on Patentability for PCT/EP2016/082861, mailed Jul. 12, 2018.
International Search Report for PCT/EP2016/082856, mailed on Mar. 28, 2017.
International Preliminary Report on Patentability for PCT/EP2016/082856, mailed Jul. 12, 2018.
International Search Report for PCT/EP2016/082860, mailed on May 3, 2017.
International Preliminary Report on Patentability for PCT/EP2016/082860, mailed on Jul. 12, 2018.
International Search Report for PCT/EP2016/082858, mailed Mar. 24, 2017.
International Preliminary Report on Patentability for PCT/EP2016/082858, mailed on Jul. 12, 2018.
International Search Report for PCT/EP2016/082855, mailed Mar. 24, 2017.
International Preliminary Report on Patentability for PCT/EP2016/082855, mailed on Jul. 12, 2018.
International Search Report for PCT/EP2016/082857, mailed May 12, 2017.
International Preliminary Report on Patentability for PCT/EP2016/082857, mailed on Jul. 12, 2018.
International Search Report for PCT/EP2016/082859, mailed on Apr. 10, 2017.
International Preliminary Report on Patentability for PCT/EP2016/082859, mailed on Jul. 12, 2018.
International Search Report for PCT/EP2018/063460, mailed on Mar. 7, 2018.
International Preliminary Report on Patentability for PCT/EP2018/063460, mailed on Dec. 5, 2019.
International Search Report for PCT/EP2018/067532, mailed on Sep. 25, 2018.
International Preliminary Report on Patentability for PCT/EP2018/067532, mailed on Jan. 9, 2020.
Office Action in Canadian Application No. 3,006,626, dated Dec. 19, 2022, in 5 pages.
Office Action in Canadian Application No. 3,006,616, dated Dec. 19, 2022, in 3 pages.
Office Action in Canadian Application No. 3,006,638, dated Jan. 17, 2023, in 4 pages.
Office Action in Canadian Application No. 3,006,627, dated Dec. 30, 2022, in 5 pages.
Office Action in Canadian Application No. 3,006,643, dated Jan. 4, 2023, in 7 pages.
Office Action in Canadian Application No. 3,006,622, dated Jan. 4, 2023, in 4 pages.
Office Action in New Zealand Application No. 742523, dated Feb. 27, 2023, in 3 pages.
Office Action in New Zealand Application No. 742538, dated Mar. 8, 2023, in 9 pages.
Office Action in New Zealand Application No. 742526, dated Mar. 13, 2023, in 8 pages.
Office Action in Australian Application No. 2018-294519, dated Mar. 10, 2023, in 3 pages.
English translation of Office Action issued in Japanese Application No. JP 2022-074131, dated Apr. 28, 2023, in 2 pages.
English translation of Office Action issued in Japanese Application No. JP 2021-116315, dated Apr. 25, 2023, in 3 pages.
Office Action in New Zealand Application No. 742526, dated Jul. 6, 2023, in 10 pages.
Office Action in Canadian Application No. 3,064,056, dated Jul. 11, 2023, in 5 pages.
English translation of Office Action issued in Japanese Application No. JP 2023-021789, dated Nov. 7, 2023, in 5 pages.
Hearing Notice dispatched on Dec. 29, 2023 in India Patent Application No. 201947041763.
Office Action with English translation in Korean application No. 10-2023-7043623, dated Apr. 18, 2024, in 12 pages.
Office Action with English translation in Japanese Application No. JP 2023-140873, mailed on Jun. 28, 2024, in 11 pages.
Office Action with English translation issued in Japanese application No. 2024-014677, mailed on Sep. 12, 2024, in 5 pages.

(56) References Cited

OTHER PUBLICATIONS

English translation of Office Action received in Japanese application No. 2023-218327, dated Oct. 18, 2024, in 5 pages.
European Search Report in application No. EP 24203896.6, dated Jan. 7, 2025, in 10 pages.

\* cited by examiner

AUTO INJECTOR WITH CHARGER SAFETY

CROSS REFERENCE TO RELATED APPLICATIONS

This application is a continuation of U.S. application Ser. No. 17/829,161, filed May 31, 2022, which is a continuation of U.S. application Ser. No. 16/060,608, filed Jun. 8, 2018, which is a U.S. National Phase Application of PCT International Application Number PCT/EP2016/082861, filed on Dec. 29, 2016, designating the United States of America and published in the English language, which is an International Application of and claims the benefit of priority to European Patent Application No. 15203173.8, filed on Dec. 30, 2015. The disclosures of the above-referenced applications are hereby expressly incorporated by reference in their entireties.

FIELD

The present disclosure relates to an auto injector, such as an electronic auto injector, and a system comprising an auto injector.

BACKGROUND

Hypodermic syringes are widely used to deliver fluids to the body. It is known to have hypodermic syringes applicable for manual operation. However, auto injectors, such as electronical auto injectors, have been developed and are widely used to aid the administering of fluid or medicaments to the body.

However, utilizing electronic means causes a risk of the electric current passing through the body, thereby causing electric shock in the user. Especially since conventional hypodermic needles are made of metal and thus electrically conductive. Electric shock may cause serious injury, which may be potentially life threatening, especially if the device is coupled to the main power grid.

Safety is an important issue, especially in the field of medical devices, such as auto injectors. Therefore, precautionary measures are needed to prevent or reduce the risk of causing electrical shock in users of an auto injector. Furthermore, precautionary measures are subject of industry standards, such as ISO 11608 and IEC 60601 relating to needle-based injection systems for medical use and medical electrical equipment.

US 2015/0320932 discloses a drug delivery device comprising a safety mechanism arranged to prevent access to a port whilst an injection needle is in fluid communication with a cartridge retained in the body of the device, and arranged to prevent establishing a fluid communication between an injection needle and the cartridge whilst the port is accessible.

However, in other auto injector systems, the cartridge may be exchangeable, such as disposable, and a needle may be attached to the cartridge prior to insertion of the cartridge into the auto injector.

SUMMARY

Despite the known solutions there is a need for an auto injector having an improved safety feature in order to prevent or reduce the risk of electric shock in users of an auto injector. In particular, there is a need for an improved safety feature in an auto injector to be used with exchangeable cartridges, such as disposable cartridges.

It is an object of the present disclosure to provide an auto injector, such as an electronic auto injector, and a system, which overcomes at least some of the disadvantages of prior art devices.

Accordingly an auto injector is provided, such as an auto injector for administering a medicament, wherein the auto injector is connectable to an electrical power supply, such as a main power socket, a USB port, a laptop, and/or an external battery. The auto injector comprises: a housing, a cartridge receiver, and an ejector member.

The housing accommodates a battery and a first electrical connector accessible via a connector opening in the housing. The first electrical connector accepts a second electrical connector of the electrical power supply.

The cartridge receiver is configured to receive a cartridge containing the medicament.

The ejector member is movable along a longitudinal axis between a first ejector position and a second ejector position. The ejector member is configured to follow movement of the cartridge along the longitudinal axis when the cartridge is received in the cartridge receiver.

The auto injector further comprises a blocking member coupled to the ejector member. The blocking member is configured to move between a blocking position wherein the connector opening is blocked and a non-blocking position wherein the connector opening is not blocked. The blocking member is in the blocking position when the ejector member is in the second ejector position. The blocking member is in the non-blocking position when the ejector member is in the first ejector position.

Also disclosed is a system comprising the auto injector and a cartridge containing the medicament. The cartridge is configured to be received in the cartridge receiver.

It is an advantage of the present disclosure that it provides blocking of the connector opening, thereby preventing connection to an external electrical power supply, such as the main grid, when a cartridge is received in the auto injector.

It is a further advantage of the present disclosure that it provides restriction of insertion of a cartridge if the auto injector is connected to an external electrical power supply, such as the main grid.

Effectively, it is an advantage of the present disclosure that it provides for a safety mechanism in an auto injector reducing the risk of serious electric shock in users of the auto injector. It is an advantage of the present disclosure that it, in an auto injector, may prevent simultaneous presence of a needle and connection to an external electrical power supply.

It is a further advantage of the present disclosure that it provides a safety mechanism which, independently of the user chosen sequence, prevents simultaneous connection to an external electrical power supply, such as the main grid, e.g. via a charger, and usage of the auto injector for administering medicament.

It is a further advantage of the present disclosure that since the ejector member is configured to follow movement of the cartridge along the longitudinal axis, the insertion of the cartridge is determinant for whether or not the connector opening is blocked or not. Thereby the disclosure provides for a safety feature, in particular advantageous for an auto injector for exchangeable cartridges, such as disposable cartridges and/or where a needle is attached to the cartridge prior to insertion of the cartridge into the auto injector.

It is envisaged that any embodiments or elements as described in connection with any one aspect may be used with any other aspects or embodiments, mutatis mutandis.

The housing has a connector opening. The connector opening may be a hole in the housing. The connector opening may be configured to allow passage of the second electrical connector, such as to allow access to the first electrical connector. The connector opening may be sized to the first and/or second electrical connector.

The auto injector comprises a battery. The housing accommodates the battery. The battery of the auto injector may be a rechargeable battery. For example, the battery may be a Li-ion battery or a NiCd battery or a NiMH battery. The battery may be configured to be charged by connection of the first electrical connector and the second electrical connector.

The first electrical connector accepts the second electrical connector. The second electrical connector electrically connects the first electrical connector to the electrical power supply. Connection of the first electrical connector and the second electrical connector may provide charging of the battery, such as by providing electrical power from the electrical power supply to the battery. The first electrical connector and/or the second electrical connector may be a USB compliant connector. The first electrical connector may be a female connector. The second electrical connector may be a male connector.

The cartridge may comprise a cartridge compartment. The cartridge compartment may be configured for containing the medicament. The cartridge compartment may contain the medicament.

The cartridge may be made of glass, and/or polymer.

The cartridge may comprise a cartridge outlet, e.g. at a first cartridge end. The cartridge outlet may be configured for fluid communication with the compartment, e.g. at the first cartridge end. The cartridge may be configured to expel medicament through the cartridge outlet. The cartridge outlet may be configured to be coupled with a needle, such as a hypodermic needle, to provide the medicament to be expelled through the needle.

The cartridge may comprise a first stopper movable inside the cartridge compartment, e.g. in a first stopper direction towards the first cartridge end. For example, the medicament may be expelled through the cartridge outlet upon movement of the first stopper, e.g. in the first stopper direction.

The cartridge may comprise a cartridge back face, e.g. at a second cartridge end, such as opposite the cartridge outlet. The cartridge back face may comprise a cartridge back end opening. The cartridge back end opening may provide access for the plunger rod to the first stopper.

The cartridge receiver may be configured to receive the cartridge through a cartridge receiver opening. Thus, the cartridge may be inserted in the cartridge receiver through the cartridge receiver opening. The cartridge receiver may be configured to receive the cartridge through a cartridge receiver opening in a cartridge receiving direction. The cartridge receiving direction may be along the longitudinal axis.

The auto injector may comprise an ejector comprising the ejector member. The ejector may be configured to eject the cartridge from the cartridge receiver.

The ejector member may have an ejector abutment face. The ejector abutment face may be configured to abut a face of the cartridge, such as the cartridge back face. The cartridge back face may abut the ejector abutment face upon insertion of the cartridge in the cartridge receiver. The ejector member may be moved towards the second ejector position, such as in the receiving direction, by insertion of the cartridge in the cartridge receiver, e.g. by movement of the cartridge back face in the receiving direction causing movement of the ejector abutment face in the receiving direction.

The ejector member may be in the first ejector position when the cartridge is not received in the cartridge receiver. The ejector member may be in the second ejector position when the cartridge is received in the cartridge receiver.

The auto injector and/or the ejector of the auto injector may comprise an ejector resilient member. The ejector resilient member may be configured to exert a force on the ejector member. The ejector resilient member may be configured to bias the ejector member towards the first ejector position, e.g. opposite the receiving direction.

The auto injector and/or the ejector of the auto injector may comprise an ejector lock. The ejector lock may be configured to restrict movement of the ejector member, such as along the longitudinal axis.

The auto injector comprises a blocking member. The blocking member may be configured to close and/or block the connector opening. The blocking member is configured to move between a blocking position and a non-blocking position. In the blocking position the connector opening is blocked, e.g. access to the first electrical connector, such as for the second electrical connector, is prevented and/or restricted, and a non-blocking position wherein the connector opening is not blocked, e.g. access to the first electrical connector, such as for the second electrical connector, is allowed and/or not prevented and/or not restricted.

The blocking member may be movable by a translational movement between the blocking position and the non-blocking position. Alternatively or additionally, the blocking member may be movable by a rotational movement between the blocking position and the non-blocking position. The blocking member may be movable between the blocking position and the non-blocking position along the longitudinal axis. Alternatively, the blocking member may be movable between the blocking position and the non-blocking position perpendicular to the longitudinal axis. For example, the blocking member may be rotationally moved around the longitudinal axis between the blocking position and the non-blocking position.

The blocking member may be a door, such as a sliding door. The blocking member, e.g. in the blocking position, may completely block the connector opening. Alternatively, the blocking member, e.g. in the blocking position, may partially block the connector opening.

The blocking member may be configured to block the connector opening when a cartridge is received in the cartridge receiver. Alternatively or additionally, the blocking member may be configured to prevent insertion of a cartridge in the cartridge receiver when the first electrical connector and the second electrical connector are connected, such as when an electrical connector, such as the second electrical connector, is inserted through the connector opening. For example, the blocking member may be prevented to move to the blocking position if the first electrical connector is coupled to the second electrical connector. For example, the movement of the blocking member may be prevented by the first and/or second electrical connector, e.g. the first and/or second electrical connector may obstruct the path of movement of the blocking member towards the blocking position.

Insertion of the cartridge in the cartridge receiver may cause movement of the blocking member. For example, the blocking member may be coupled to the ejector member, such as to translate movement of the ejector member to the blocking member. Insertion of the cartridge in the cartridge receiver may move the ejector member, and movement of the ejector member may cause movement of the blocking member. Thus, insertion of the cartridge in the cartridge receiver may cause movement of the blocking member. Alternatively or additionally, the ejector member may be prevented to move to the second ejector position if the blocking member is prevented to move to the blocking position, e.g. if the first electrical connector is coupled to the second electrical connector. Thus, insertion of the cartridge in the cartridge receiver may be prevented if the first electrical connector is coupled to the second electrical connector.

The blocking member may comprise a first blocking coupling member. The ejector member may comprise a second blocking coupling member. The first blocking coupling member and the second blocking coupling member may be in engagement to translate movement of the ejector member to the blocking member. The first blocking coupling member may comprise a slot and/or a protrusion. The second blocking coupling member may comprise a protrusion and/or a slot. The second blocking coupling member and the first blocking coupling member may be movably connected. The second blocking coupling member and/or the first blocking coupling member may allow an amount of clearance, such that only part of movement of the ejector is translated to movement of the blocking member.

Movement of the ejector member from a third ejector position to the second ejector position may move, and/or cause movement of, the blocking member from the non-blocking position to the blocking position. The third ejector position may be between the first ejector position and the second ejector position. For example, the ejector member may move from the first ejector position towards the second ejector position, such as upon insertion of a cartridge in the cartridge receiver, and from the third ejector position, located between the first ejector position and the second ejector position, the movement of the ejector member is transmitted to the blocking member, such that the blocking member moves towards the blocking position.

Alternatively or additionally, movement of the ejector member from a fourth ejector position to the first ejector position moves the blocking member from the blocking position to the non-blocking position. The fourth ejector position may be between the first ejector position and the second ejector position. The fourth ejector position may be the third ejector position. For example, the ejector member may move from the second ejector position towards the first ejector position, such as upon removal of the cartridge from the cartridge receiver, and from the fourth ejector position, located between the first ejector position and the second ejector position, the movement of the ejector member is transmitted to the blocking member, such that the blocking member moves towards the non-blocking position.

The second blocking coupling member comprising a slot and/or a protrusion and the first blocking coupling member comprising a protrusion and/or a slot may allow an amount of clearance and facilitate such exemplified transmission of movement.

The blocking member and/or the first blocking coupling member of the blocking member, may comprise a first blocking member stop and a second blocking member stop. For example, the first blocking coupling member may comprise a slot comprising the first blocking member stop and the second blocking member stop. The second blocking coupling member may comprise a protrusion arranged to catch the first blocking member stop by movement in one direction along the longitudinal axis, and arranged to catch the second blocking member stop by movement in another direction along the longitudinal axis. For example, the second blocking coupling member may catch the first blocking member stop upon movement of the ejector member towards the first ejector position, such as upon removal of the cartridge from the cartridge receiver. The second blocking coupling member may catch the second blocking member stop upon movement of the ejector member towards the second ejector position, such as upon insertion of the cartridge in the cartridge receiver.

Alternatively or additionally, the ejector member, and/or the second blocking coupling member of the ejector member, may comprise a first blocking member stop and a second blocking member stop. For example, the second blocking coupling member may comprise a slot comprising the first blocking member stop and the second blocking member stop. The first blocking coupling member may comprise a protrusion arranged to catch the first blocking member stop by movement in one direction along the longitudinal axis, and arranged to catch the second blocking member stop by movement in another direction along the longitudinal axis. For example, the first blocking coupling member may catch the first blocking member stop upon movement of the ejector member towards the first ejector position, such as upon removal of the cartridge from the cartridge receiver. The first blocking coupling member may catch the second blocking member stop upon movement of the ejector member towards the second ejector position, such as upon insertion of the cartridge in the cartridge receiver.

Providing such non-fixed coupling between the ejector member and the blocking member provides for a shorter device, as it converts a long sliding movement, e.g. of the ejector member, to a shorter one, e.g. of the blocking member.

Alternatively, the first blocking coupling member and the second blocking coupling member may be fixedly connected. For example, the ejector member and the blocking member are fixedly connected with respect to movement along the longitudinal axis.

Movement of the ejector member to the second ejector position may require movement of the blocking member to the blocking position. For example, if the blocking member is prevented from moving to the blocking position, e.g. if the second electrical connector is coupled to the first electrical connector, the movement of the ejector member to the second ejector position is restricted and/or impossible. Thereby it may be prevented that a cartridge is received by the cartridge receiver if the second electrical connector is connected, e.g. if a charger is connected to the auto injector to charge the battery.

The auto injector may comprise a plunger rod, such as a plunger rod configured to eject medicament from the cartridge. The plunger rod may be configured to advance a first stopper of the cartridge to expel medicament through the cartridge outlet.

The auto injector may comprise a drive module. The drive module may be coupled to actuate a plunger rod, such as the plunger rod of the auto injector. The drive module may be configured to receive electrical power from the battery. The drive module may be electrically connected to the battery for receiving electrical power. The drive module may be accommodated by the housing. The drive module may comprise a motor, such as an electro-mechanical motor, such as a DC motor, e.g. a DC motor with or without brushes. The drive module may comprise a solenoid motor. The drive module may comprise a shape memory metal engine. The drive module may comprise an arrangement of springs configured to actuate the plunger rod. The drive module may comprise a pressurized gas configured to actuate the plunger rod.

BRIEF DESCRIPTION OF THE FIGURES

A more detailed description follows below with reference to the drawing, in which.

DETAILED DESCRIPTION

Figure 1:
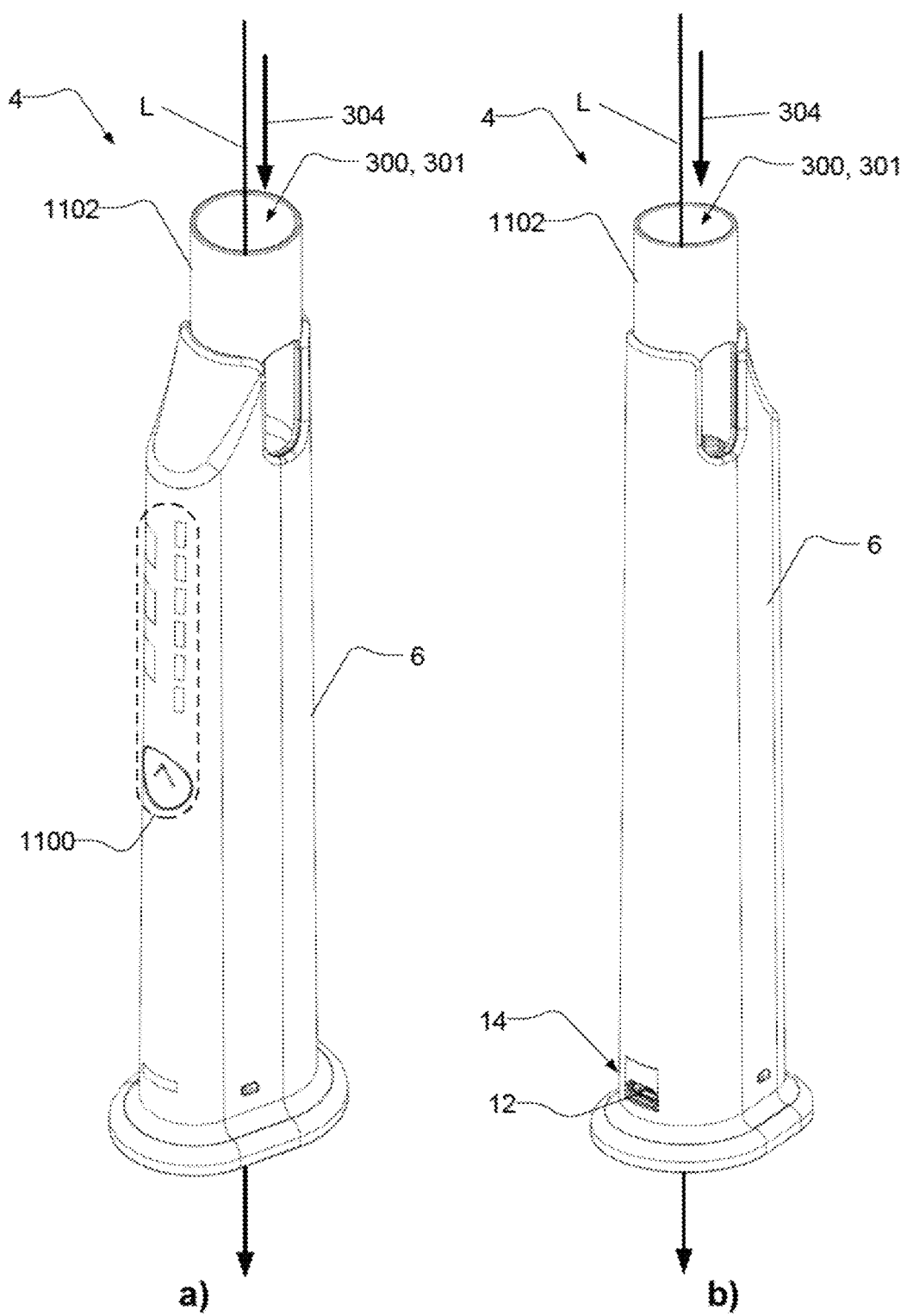
FIG. 1a-b shows an exemplary auto injector.

Various embodiments are described hereinafter with reference to the figures. Like reference numerals refer to like elements throughout. Like elements will, thus, not be described in detail with respect to the description of each figure. It should also be noted that the figures are only intended to facilitate the description of the embodiments. They are not intended as an exhaustive description of the claimed invention or as a limitation on the scope of the claimed invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

FIG. 1a and FIG. 1b show an exemplary auto injector 4. FIG. 1b shows the auto injector 4 turned 180 deg. compared to the view of FIG. 1a.

The auto injector 4 may be configured for administering a medicament. The auto injector 4 may be an electronic auto injector, e.g. the auto injector 4 may be connectable to an electrical power supply (not shown), such as an external battery or a power plug.

The auto injector 4 comprises a housing 6, and a first electrical connector 12. The first electrical connector 12 is accessible via a connector opening 14 in the housing 6. The first electrical connector 12 accepts a second electrical connector 18 (see e.g. FIG. 3).

The connection of the second electrical connector 18 and the first electrical connector 12 may for example provide charging of a battery (not visible) of the auto injector 4. The battery may be accommodated by the housing 6. Alternatively or additionally, the connection of the second electrical connector 18 and the first electrical connector 12 may provide transferring of data to/from the auto injector 4, such as to/from a memory of the auto injector 4.

The auto injector 4 comprises a cartridge receiver 300. The cartridge receiver is configured to receive a cartridge and/or a cartridge assembly comprising a cartridge. The cartridge may contain the medicament.

The cartridge receiver 300 has a cartridge receiver opening 301. The cartridge receiver 300 is configured to receive the cartridge through the cartridge receiver opening 301 in a cartridge receiving direction 304 along a longitudinal axis L.

The auto injector 4 may comprise a user interface 1100, as illustrated. The auto injector 4 may comprise contact member 1102. The contact member 1102 may be configured to be pressed against an injection site. The contact member 1102 may be movable in the cartridge receiving direction 304, relative to the housing, if pressed against the injection site. The contact member 1102 may be part of the user interface 1100.

FIG. 2a and FIG. 2b shows an exemplary system 2. The system 2 comprises an exemplary auto injector 4, as described in relation to FIG. 1, and an exemplary cartridge 700 received in the cartridge receiver 300. FIG. 2a shows a front view of the auto injector 4. FIG. 2b shows the auto injector 4 turned 180 deg. compared to the view of FIG. 2a.

The auto injector 4 comprises a blocking member 100, 100'. The blocking member is configured to move between a blocking position and a non-blocking position. In the blocking position, the connector opening 14 is blocked, e.g. closed, as illustrated. In the non-blocking position, the connector opening 14 is not blocked, e.g. open, as illustrated in FIG. 1b. In the non-blocking position a second electrical connector 18 (see e.g. FIG. 3) and the first electrical connector 12 may be connectable via the connector opening 14. In the blocking position the blocking member 100, 100' may prevent connection of a second electrical connector 18 (see e.g. FIG. 3) and the first electrical connector 12.

The blocking member 100 may be movable along the longitudinal axis L, such as movable between the blocking position and the non-blocking position along the longitudinal axis L. For example, the blocking member 100 may be a sliding element, e.g. sliding along the longitudinal axis L.

Alternatively, the blocking member 100' may be movable perpendicularly to the longitudinal axis L, such as movable between the blocking position and the non-blocking position perpendicular to the longitudinal axis L. For example, the blocking member 100' may be a rotating element, e.g. rotating about the longitudinal axis L.

The position of the blocking member 100, 100' may be determined by insertion of a cartridge 700 in the cartridge receiver 300. The blocking member 100, 100' may be in the blocking position when the cartridge 700 is received in the cartridge receiver 300, such as shown in FIG. 2b. The blocking member 100, 100' may be in the non-blocking position when the cartridge is not received in the cartridge receiver, such as shown in FIG. 1b.

Figure 3:
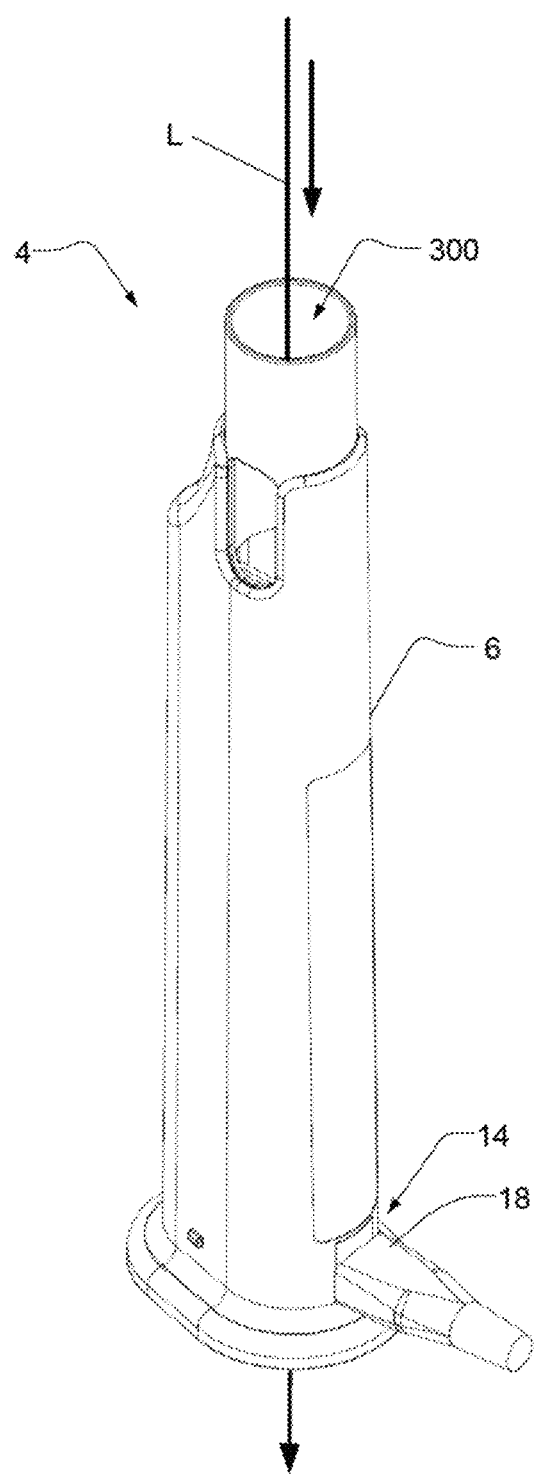
FIG. 3 shows an exemplary auto injector with an electrical connector.

FIG. 3 shows an exemplary auto injector 4, as described in relation to previous figures, wherein a second electrical connector 18 is connected to the first electrical connector. The blocking member is in the non-blocking position to allow connection of the second electrical connector 18 to the first electrical connector through the connector opening 14 of the housing 6.

The blocking member may be prevented to move to the blocking position. For example, the second electrical connector 18 may prevent the movement of the blocking member to the blocking position. For example, the second electrical connector 18 may obstruct the path of movement of the blocking member towards the blocking position.

Insertion of a cartridge in the cartridge receiver 300 may cause movement of the blocking member 100. For example, insertion of the cartridge in the cartridge receiver 300 may require movement of the blocking member to the blocking position. Thus, the blocking member being prevented from moving to the blocking position may prevent insertion of the cartridge. Thus, insertion of the cartridge in the cartridge receiver 300 may be prevented when the first electrical connector is connected to the second electrical connector 18.

Figure 4:
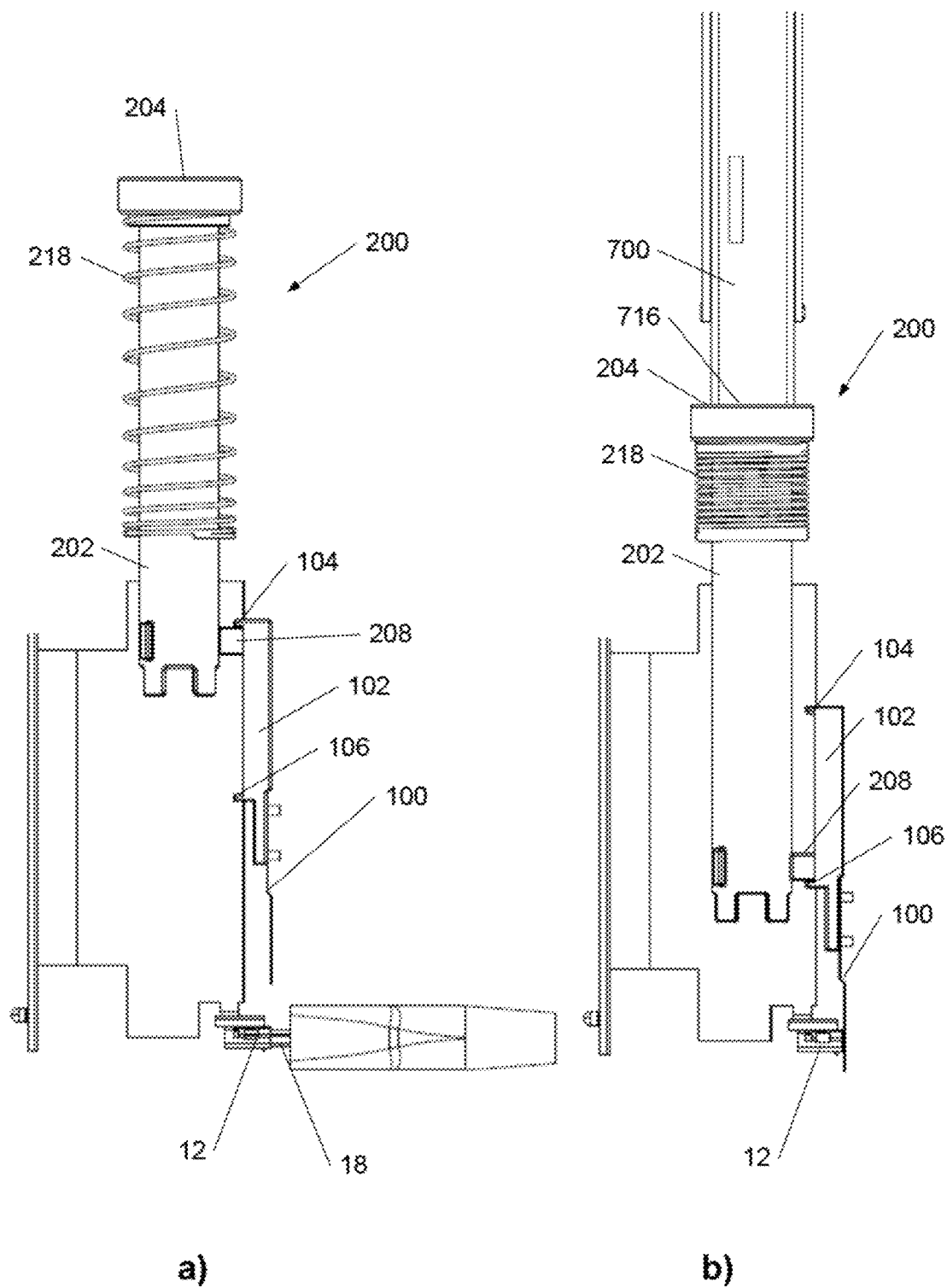
FIGS. 4a-b schematically illustrate parts of an exemplary auto injector.

FIG. 4a and FIG. 4b schematically illustrate selected parts of an exemplary auto injector as described in relation to previous figures.

FIG. 4a and FIG. 4b illustrate an ejector 200 of the auto injector. The ejector 200 comprises an ejector member 202. The ejector member 202 is movable along the longitudinal axis L. The ejector member 202 is movable between a first ejector position, shown in FIG. 4a, and a second ejector position, shown in FIG. 4b. The ejector member 202 is configured to follow movement of a cartridge 700 (only showed in part) when the cartridge 700 is received in the cartridge receiver 300 (see above figs.). As illustrated, when the cartridge 700 is received, the ejector member 202 is moved to the second ejector position. The ejector member 202 may be in the first ejector position when the cartridge 700 is not received in the cartridge receiver, as shown in FIG. 4a. The ejector member 202 may be in the second ejector position when the cartridge 700 is received in the cartridge receiver, as shown in FIG. 4b.

The ejector member 202 comprises an ejector abutment face 204. The ejector abutment face 204 is configured to abut a face, such as a cartridge back face 716, of the cartridge 700. By inserting the cartridge 700 into the cartridge receiver, the cartridge back face 716 may abut the ejector abutment face 204, and the ejector member 202 may be pushed towards the second ejector position.

The auto injector, such as the ejector 200 of the auto injector, comprises an ejector resilient member 218, such as a spring. The ejector resilient member 218 is configured to exert a force on the ejector member 202. For example, the ejector resilient member 218 may be configured to bias the ejector member 202 towards the first ejector position. For example, the ejector resilient member 218 may cause the ejector member 202 to be in the first ejector position, when a cartridge 700 is not received and/or being received in the cartridge receiver and/or being removed from the cartridge receiver. The ejector resilient member 218 may be compressed when the cartridge 700 is received in the cartridge receiver, as shown in FIG. 4b.

FIG. 4a and FIG. 4b illustrate a blocking member 100 of the auto injector. The ejector member 202 is coupled to the blocking member 100. The blocking member comprises a first blocking coupling member 102. The ejector member comprises a second blocking coupling member 208. The first blocking coupling member 102 and the second blocking coupling member 208 are in engagement to translate movement of the ejector member 202 to the blocking member 100.

The blocking member 100 is in the blocking position when the ejector member is in the second ejector position, as shown in FIG. 4b. The blocking member 100 is in the non-blocking position when the ejector member 202 is in the first ejector position, as shown in FIG. 4a.

In the non-blocking position, a second electrical connector 18 can be connected to the first electrical connector 12, as shown in FIG. 4a. In the blocking position, the blocking member 100 is positioned in front of the first electrical connector 12. Thereby, the second electrical connector 18 cannot be connected to the first electrical connector 12, when the blocking member 100 is in the blocked position.

Conversely, as seen in FIG. 4a, the blocking member 100 is not able to move to the blocking position, due to the second electrical connector 18 being connected to the first electrical connector 12. Thus, the ejector member 202 may be prevented from moving to the second ejector position. Thus, insertion of the cartridge may be prevented when the second electrical connector 18 is connected to the first electrical connector 12.

The blocking member 100 comprises a first blocking member stop 104, and a second blocking member stop 106. The first blocking coupling member 102 is formed as a slot comprising the first blocking member stop 104 and the second blocking member stop 106.

The second blocking coupling member 208 may comprise a protrusion arranged to catch the first blocking member stop 104 by movement in one direction, and arranged to catch the second blocking member stop 106 by movement in another direction, e.g. along the longitudinal axis. For example, the second blocking coupling member 208 may catch the first blocking member stop 104, as shown in FIG. 4a, upon movement of the ejector member towards the first ejector position, such as upon removal of the cartridge 700 from the cartridge receiver. The second blocking coupling member 208 may catch the second blocking member stop 106, as shown in FIG. 4b, upon movement of the ejector member towards the second ejector position, such as upon insertion of the cartridge 700 in the cartridge receiver.

Figure 2:
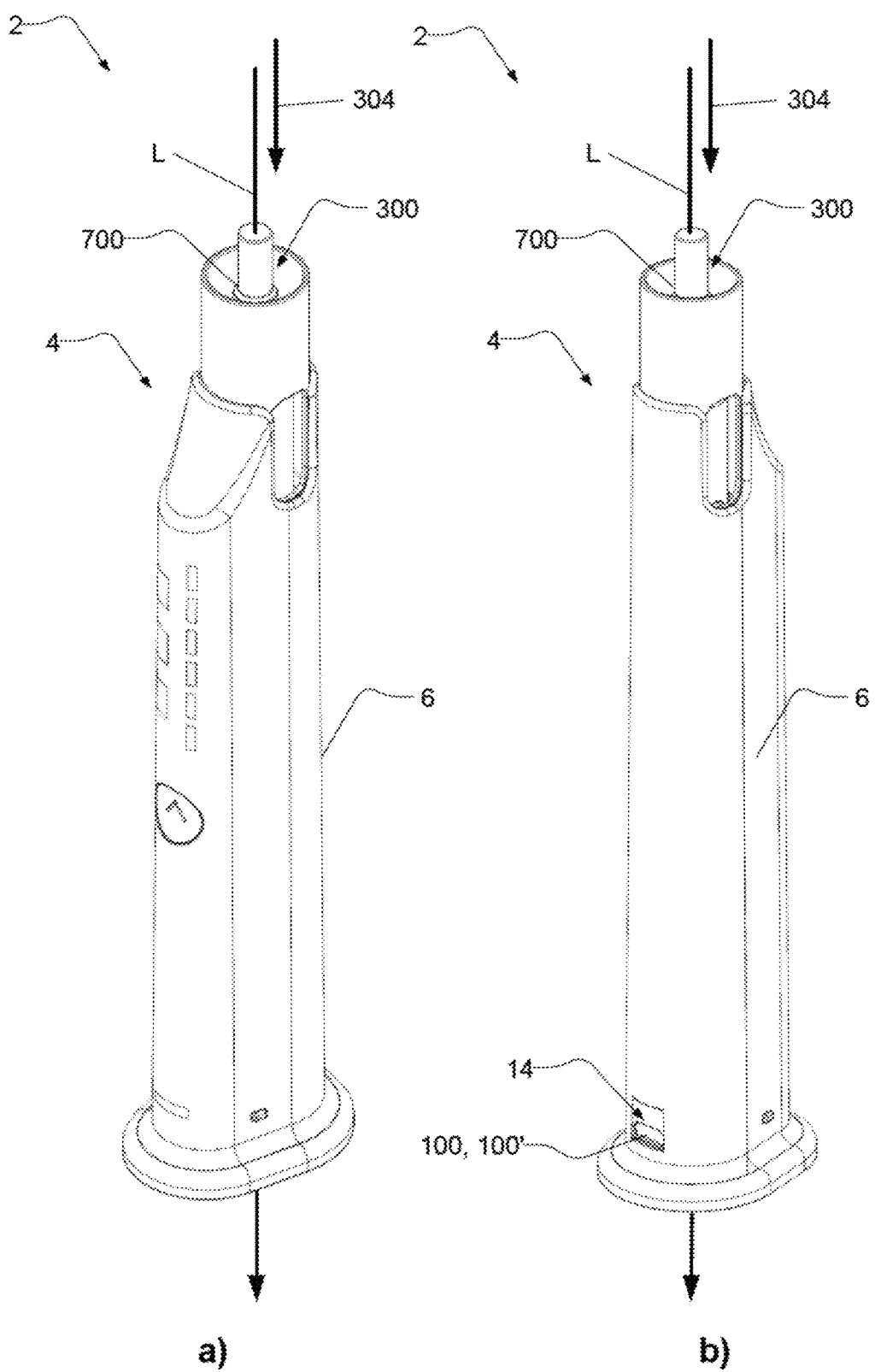
FIG. 2a-b shows an exemplary auto injector with an exemplary cartridge.

FIGS. 5a-5d schematically illustrate insertion and removal of an exemplary cartridge in an exemplary auto injector 4, such as the auto injector as described in relation to FIGS. 1-3. FIGS. 5a-5d only show selected parts of the exemplary auto injector 4.

The auto injector 4 comprises a first electrical connector 12, and a cartridge receiver 300 configured to receive a cartridge 700.

The auto injector 4 comprises an ejector member 202 and an ejector resilient member 218. The ejector member 202 comprises an ejector abutment face 204 configured to abut a face, such as a cartridge back face 716, of the cartridge 700. The auto injector further comprises a blocking member 100 coupled to the ejector member 202. In the example depicted, the ejector member 202 and the blocking member 100 are fixedly connected. The blocking member 100 is configured to block a connector opening to the first electrical connector 12, e.g. when the blocking member is in a blocked position.

Also illustrated in FIGS. 5a-5d is a cartridge assembly 600 comprising the cartridge 700. The cartridge 700 comprises a cartridge compartment 702. The cartridge compartment 702 may containing a medicament, or be configured to contain a medicament. The cartridge comprises a cartridge back face 716 configured to abut the ejector abutment face 204 of the ejector member 202.

The cartridge assembly 600 comprises a needle assembly 900. The needle assembly 900 comprises a needle 902, such as a hypodermic needle, and a needle cover 908. The needle cover 908 is covering the needle 902 such as to avoid contact with the needle 902. The needle cover 908 is removable. The needle cover 908 may be removed prior to initiating the injection of medicament.

Figure 5:
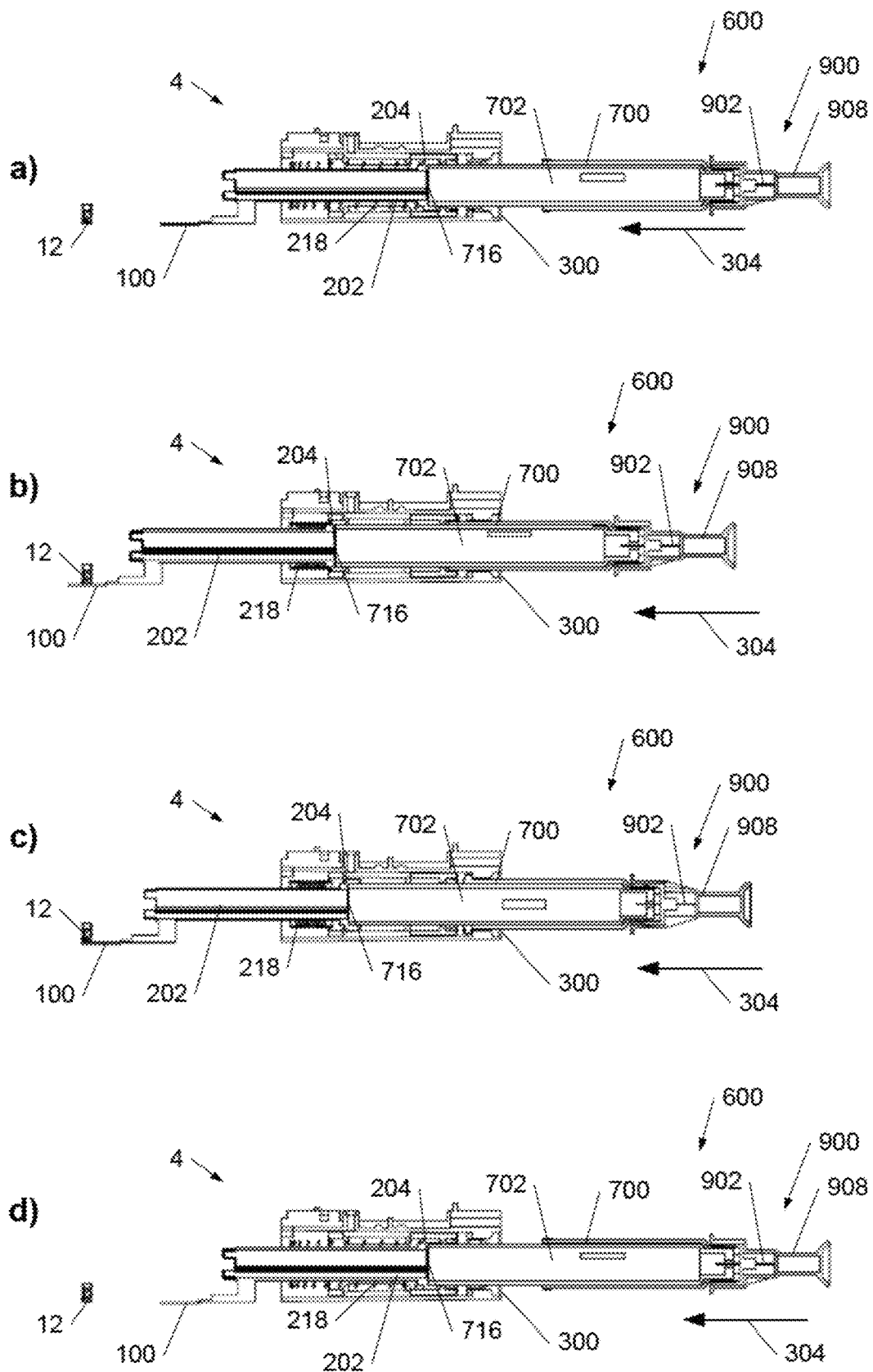
FIGS. 5a-d schematically illustrate insertion and removal of an exemplary cartridge in an exemplary auto injector.

FIG. 5a shows a first situation, wherein the cartridge 700 is about to be received in the cartridge receiver 300 in the cartridge receiving direction 304. The cartridge back face 716 has abutted the ejector abutment face 204. The ejector member 202 is in the first ejector position. The blocking member 100 is in the non-blocking position.

FIG. 5c shows a second situation following the first situation, wherein the cartridge 700 is moved to be received in the cartridge receiver 300. The cartridge 700 may be retained in the cartridge receiver 300 when received in the cartridge receiver 300. The cartridge receiver 300 is configured to selectively retain the cartridge 700 in the cartridge receiver 300. The ejector member 202 is in the second ejector position, and the blocking member 100 is in the blocking position. The ejector resilient member 218 is compressed. The cartridge 700 being retained in the cartridge receiver 300 prevents the ejector resilient member 218 from causing the ejector member 202 to move towards the first ejector position.

In case a second electrical connector had been connected to the first connector 12, the blocking member 100 would be prevented from moving to the blocking position, and thus, the ejector member 202 would be prevented from moving to the second ejector position, since the ejector member 202 and the blocking member 100 are connected. Thus, the cartridge 700 would not be able to be received in the cartridge receiver 300, e.g. so as to be retained in the cartridge receiver 300, if the second electrical connector had been connected to the first connector 12.

FIG. 5b shows an optional third situation between the first situation and the second situation, wherein the cartridge 700 is pushed further into the cartridge receiver 300 in the cartridge receiving direction 304. The ejector member is moved passed the second ejector position. The ejector resilient member 218 is compressed, and the blocking member 100 is moved passed the blocking position. This situation illustrates an example of how the cartridge receiver 300 may selectively retain the cartridge 700 in the cartridge receiver 300.

For example, the cartridge receiver 300 may retain the cartridge 700 following the cartridge 700 being pushed in the cartridge receiving direction causing movement of the ejector member passed the second ejector position a first time. The cartridge receiver 300 may release the cartridge 700 following the cartridge 700 being pushed in the cartridge receiving direction and causing movement of the ejector member passed the second ejector position a second time.

FIG. 5d shows a fourth situation, wherein the cartridge 700 is released from the cartridge receiver 300 and moved opposite the cartridge receiving direction 304 by the ejector resilient member 218 expanding. The ejector resilient member 218 causes the ejector member 202 to move towards the first ejector position. The retention members of the cartridge receiver 300 does not prevent movement of the cartridge 700, and the ejector resilient member 218 causes the ejector member 202 to move towards the first ejector position. By moving the ejector member 202 to the first ejector position, the blocking member 100 is moved to a non-blocking position. Thus, connection of a second electrical connector to the first electrical connector 12 is again possible.

Releasing the cartridge 700 from the cartridge receiver 300 may involve moving the cartridge in the cartridge receiving direction 304 as described in relation to FIG. 5b. Thus, the optional situation shown in FIG. 5b may optionally also be inserted between the situations of FIGS. 5c and 5d.

FIGS. 6a-6f schematically illustrate an exemplary coupling between a blocking member 100 and an ejector member 202. Such as blocking member 100 and ejector member 202 of an exemplary auto injector, such as the auto injector as described in relation to FIGS. 1-3. FIGS. 6a-6f only show selected parts of the exemplary auto injector.

The auto injector, such as an ejector of the auto injector, comprises an ejector resilient member 218, such as a spring. The ejector resilient member 218 is configured to exert a force on the ejector member 202. For example, the ejector resilient member 218 may be configured to bias the ejector member 202 towards a first ejector position. The ejector member 202 may be movable between a first ejector position and a second ejector position. The first ejector position may be the position of the ejector member 202 when no cartridge is received in the cartridge receiver. The second ejector position may be the position of the ejector member 202 when a cartridge is received in the cartridge receiver. The ejector member 202 may be in other positions, such as a third ejector position and/or a fourth ejector position. The third ejector position and/or the fourth ejector position may be between the first ejector position and the second ejector position.

The blocking member 100 is configured to block a connector opening to the first electrical connector 12, e.g. when the blocking member is in a blocked position.

The ejector member 202 is coupled to the blocking member 100. The blocking member comprises a first blocking coupling member 102. The ejector member comprises a second blocking coupling member 208. The first blocking coupling member 102 and the second blocking coupling member 208 are in engagement to translate movement of the ejector member 202 to movement of the blocking member 100.

The blocking member 100 comprises a first blocking member stop 104, and a second blocking member stop 106. The first blocking coupling member 102 is formed as a slot comprising the first blocking member stop 104 and the second blocking member stop 106. The second blocking coupling member 208 is arranged to catch the second blocking member stop 106 by movement in one direction, e.g. in the cartridge receiving direction 304, and arranged to catch the first blocking member stop 104 by movement in an opposite direction, e.g. opposite the cartridge receiving direction 304.

Figure 6:
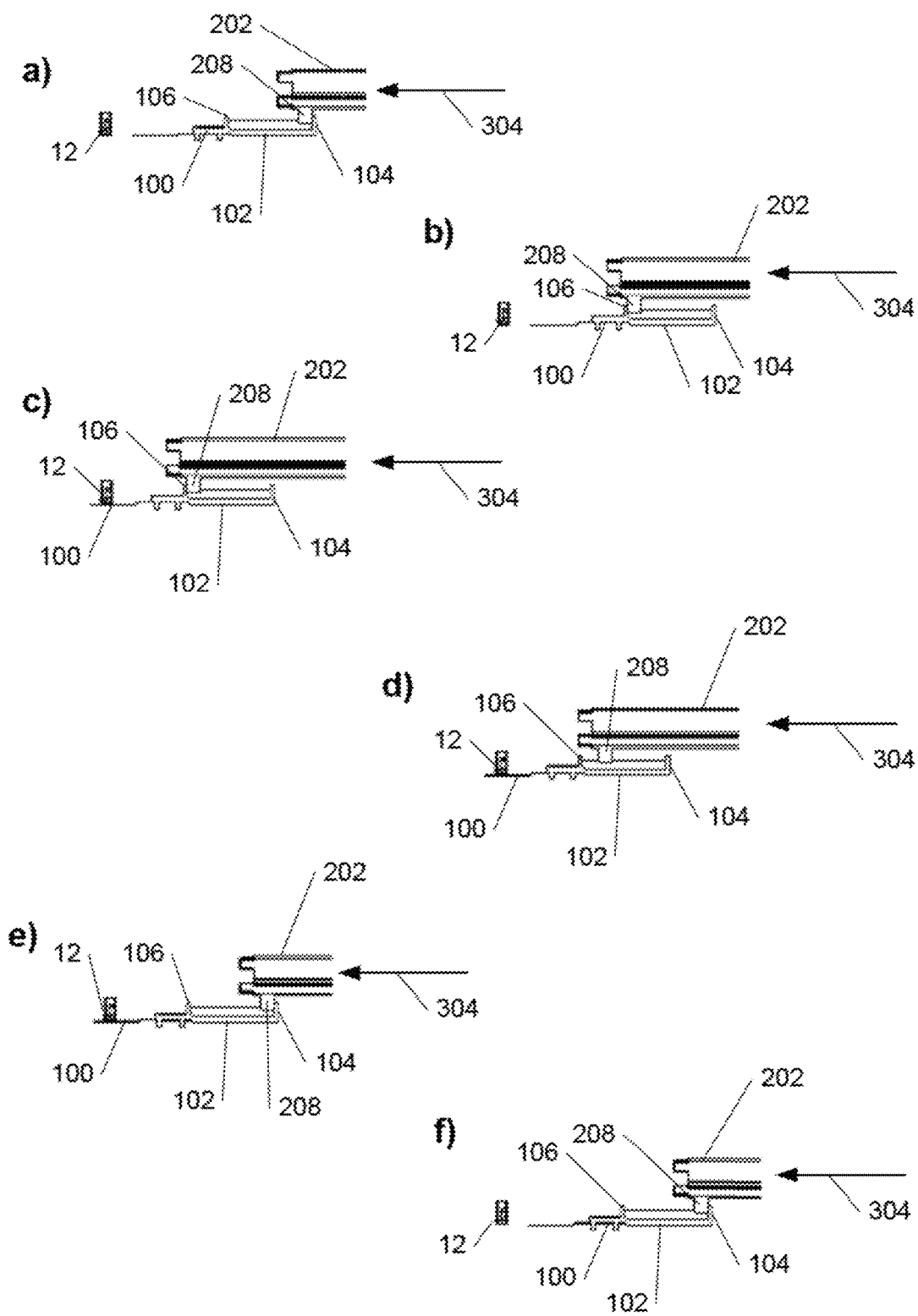
FIGS. 6a-f schematically illustrate an exemplary coupling between a blocking member and an ejector member.

FIG. 6a shows a first situation, e.g. when no cartridge is received in the cartridge receiver. The ejector member 202 is in the first ejector position, and the blocking member 100 is in the non-blocking position. Thus, a second electrical connector may be connected to the first electrical connector 12.

FIG. 6b shows a second situation, e.g. wherein a cartridge is being received in the cartridge receiver. The ejector member 202 is in the third ejector position. Compared to the previous figure, the ejector member 202 has moved in the cartridge receiving direction 304, e.g. caused by insertion of a cartridge in the cartridge receiver. The second blocking coupling member 208 abuts the second blocking member stop 106. Thus, from the third ejector position, movement of the ejector member 202 in the cartridge receiving direction 304 will result in movement of the blocking member 100 in the cartridge receiving direction 304.

FIG. 6c shows a third situation, e.g. wherein the cartridge has been further pushed in the cartridge receiving direction 304, e.g. for receiving the cartridge in the cartridge receiver. The ejector member 202 is in the second ejector position. The blocking member 100 is in the blocking position. Comparing with the previous figure, the ejector member 202 has moved, e.g. caused by the cartridge being received in the cartridge receiver, in the cartridge receiving direction 304. The second blocking coupling member 208 has moved with the ejector member 202, and by abutment with the second blocking member stop 106 the movement of the ejector member 202 to the second ejector position has caused the blocking member 100 to move to the blocking position.

FIG. 6d shows a fourth situation, wherein the ejector member 202 is in a position, wherein second coupling member 208 does not abut any of the first blocking member stop 104 or the second blocking member stop 106. For example, such a position may be between the second ejector position and the third ejector position and/or the fourth ejector position. For example, the ejector member 202 may be in such a position after the cartridge has been received in the cartridge receiver. In the illustrated situation, e.g. in the illustrated position of the ejector member 202, movement of the ejector member 202 does not immediately translate into movement of the blocking member. The engagement of the first blocking coupling member 102 and the second blocking coupling member 208 allows a distance of slack between movement of the ejector member 202 and the blocking member 100.

FIG. 6e shows a fifth situation, e.g. wherein the cartridge is being released from the cartridge receiver, thus being moved opposite the cartridge receiving direction 304. The ejector member 202 is in the fourth ejector position. The blocking member is in the blocking position. Compared to the previous figure, the ejector member 202 has moved opposite the cartridge receiving direction 304 to the fourth ejector position, e.g. caused by the ejector resilient member (see previous figs.). The second blocking coupling member 208 abuts the first blocking member stop 104. Thus, from the fourth ejector position, movement of the ejector member 202 opposite the cartridge receiving direction 304 will result in movement of the blocking member 100 opposite the cartridge receiving direction 304.

FIG. 6f shows a sixth situation, e.g. wherein the cartridge has been removed from the cartridge receiver. The ejector member 202 is in the first ejector position. The blocking member 100 is in the non-blocking position. Comparing with the previous figure, the ejector member 202 has moved, e.g. caused by the ejector resilient member (see previous figs.) and the cartridge being removed from the cartridge receiver. The second blocking coupling member 208 has moved with the ejector member 202, and by abutment with the first blocking member stop 104 the movement of the ejector member 202 to the first ejector position has caused the blocking member 100 to move to the non-blocking position.

Figure 7:
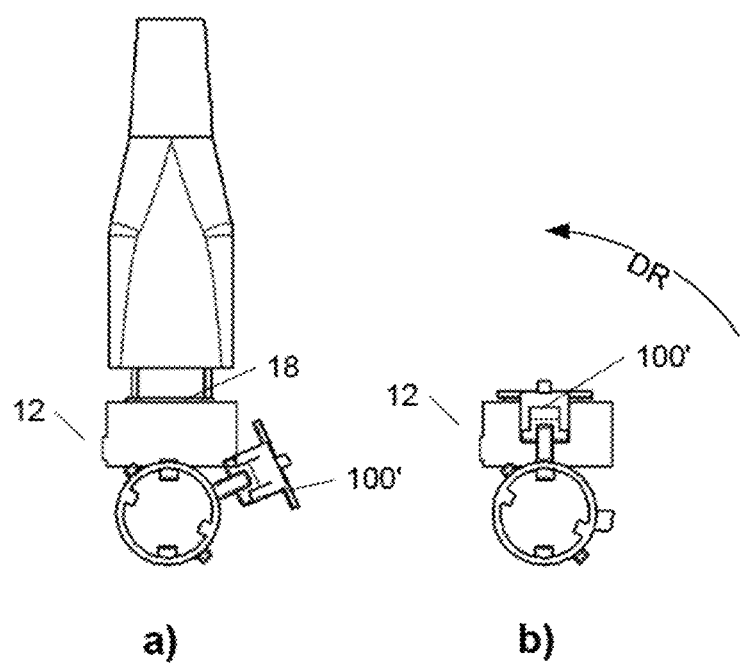
FIGS. 7a-b schematically illustrate an exemplary blocking member.

FIG. 7a and FIG. 7b show an exemplary blocking member 100' of an exemplary auto injector, such as the auto injector of FIGS. 1-3. The blocking member 100' as illustrated in FIG. 7a and FIG. 7b is a rotational blocking member. The blocking member 100' is configured to rotate in a direction of rotation DR in response to translational movement of the ejector member in the cartridge receiving direction.

FIG. 7a shows the blocking member 100' being in the non-blocking position. A second electrical connector 18 is connected to the first electrical connector 12.

FIG. 7b shows the blocking member 100' being in the blocking position. Connection of a second electrical connector to the first electrical connector 12 is prevented by the blocking member 100'. Compared to FIG. 7a, the blocking member 100' has been rotated in the direction of rotation DR, to the blocking position.

Figure 8:
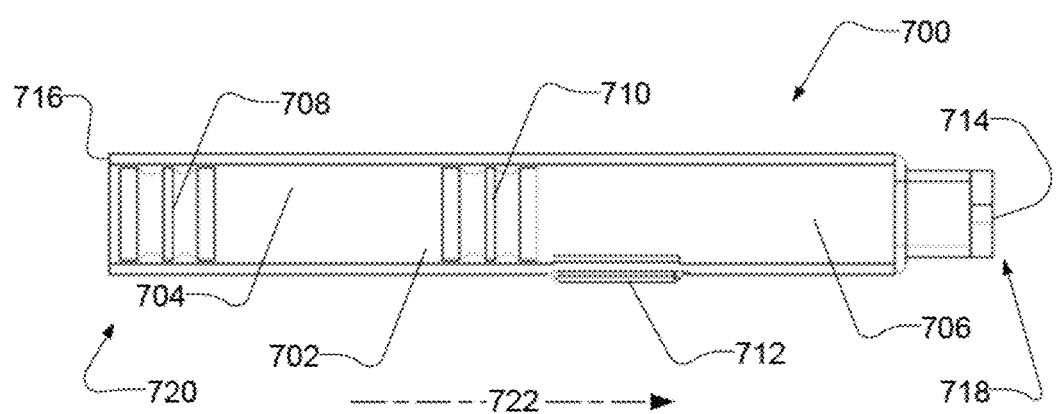
FIG. 8 schematically illustrates an exemplary cartridge.

FIG. 8 schematically illustrates an exemplary cartridge 700, such as a cartridge 700 being configured to be received in the cartridge receiver of an auto injector, such as the auto injector described in relation to previous figures.

The cartridge 700 comprises a cartridge compartment 702. The cartridge compartment 702 may be configured for containing a medicament. The cartridge 700 has a first end 718 and a second end 720. The cartridge 700 comprises a cartridge outlet 714 at the first cartridge end 718. The cartridge may be configured to expel medicament through the cartridge outlet 714.

The cartridge comprises a first stopper 708 movable inside the cartridge compartment, e.g. in a first stopper direction 722, e.g. towards the first cartridge end. For example, the medicament may be expelled through the cartridge outlet 714 upon movement of the first stopper 708 in the first stopper direction. The cartridge comprises a cartridge back face 716 at the second cartridge end. The cartridge back face 716 comprises a cartridge back end opening for providing access to the first stopper 708 for a plunger rod.

As illustrated, the cartridge 700 may be a dual chamber cartridge. The cartridge comprises a second stopper 710 movable inside the cartridge compartment 702, e.g. in the first stopper direction 722, e.g. towards the first cartridge end. The cartridge compartment 702 comprises a first cartridge subcompartment 704 and a second cartridge subcompartment 706. The first cartridge subcompartment 704 is between the first stopper 708 and the second stopper 710. The second cartridge subcompartment 706 is between the second stopper 710 and the cartridge outlet 714. The cartridge comprises a bypass section 712 for providing fluid communication between the first cartridge subcompartment and the second cartridge subcompartment. The bypass section 712 provides fluid communication between the first cartridge subcompartment and the second cartridge subcompartment when the second stopper 710 is positioned in the bypass section 712.

Figure 9:
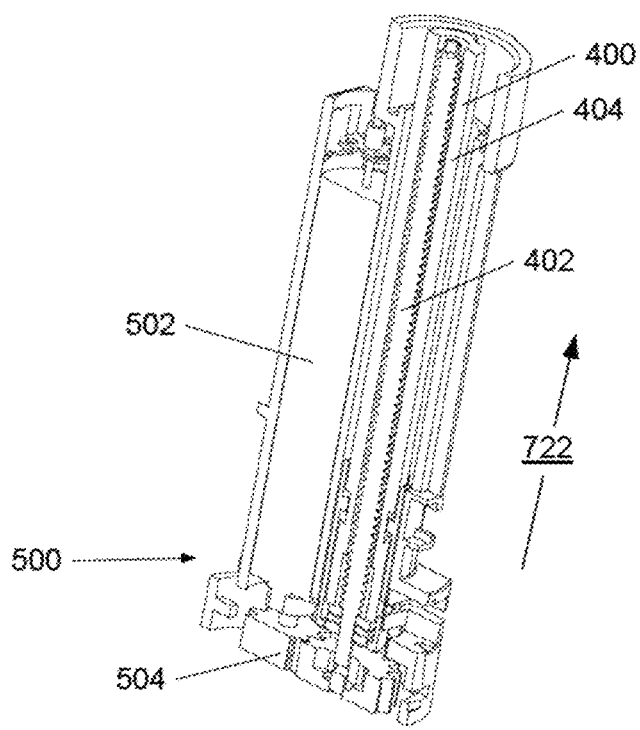
FIG. 9 schematically illustrates an exemplary drive module and plunger rod.

FIG. 9 schematically illustrates an exemplary drive module 500 and plunger rod 400. Such as a drive module 500 and a plunger rod 400 for an auto injector as described in relation to previous figures.

The plunger rod 400 is configured to advance a first stopper of a cartridge, such as a cartridge described in relation to FIG. 8, such as a cartridge received in the auto injector, such as received in the cartridge receiver of the auto injector. The plunger rod 400 comprises an outer plunger rod 404 with an inner thread, and an inner plunger rod 402 with an outer thread. The thread of the inner plunger rod 402 is in engagement with the thread of the outer plunger rod 404. The outer plunger rod 404 is prevented from rotating relative to the housing of the auto injector. The movement of the plunger rod 400 comprises rotation of the inner plunger rod 402. The rotation of the inner plunger rod 402 results in translational movement of the outer plunger rod 404, due to the outer plunger rod 404 being prevented from rotating. The outer plunger rod 404, when moved translationally in the first stopper direction 722, is configured to abut the first stopper of the cartridge, and to move the first stopper in the first stopper direction 722.

The drive module 500 is coupled to actuate the plunger rod 400. The drive module 500 is electrically connected to a battery for receiving electrical power. The drive module 500 comprises a motor 502, such as an electro-mechanical motor, such as a DC motor. The drive module 500 comprises a transmission 504 for coupling the motor 502 to the inner plunger rod 402 of the plunger rod 400.

Although the example shown comprises a motor 502, which may be an electro-mechanical motor, it will be readily understood that the auto injector 4 may be realised having an alternative drive module, such as comprising a solenoid motor, a shape memory metal engine, an arrangement of springs and/or a pressurized gas configured to actuate the plunger rod 400.

Figure 10:
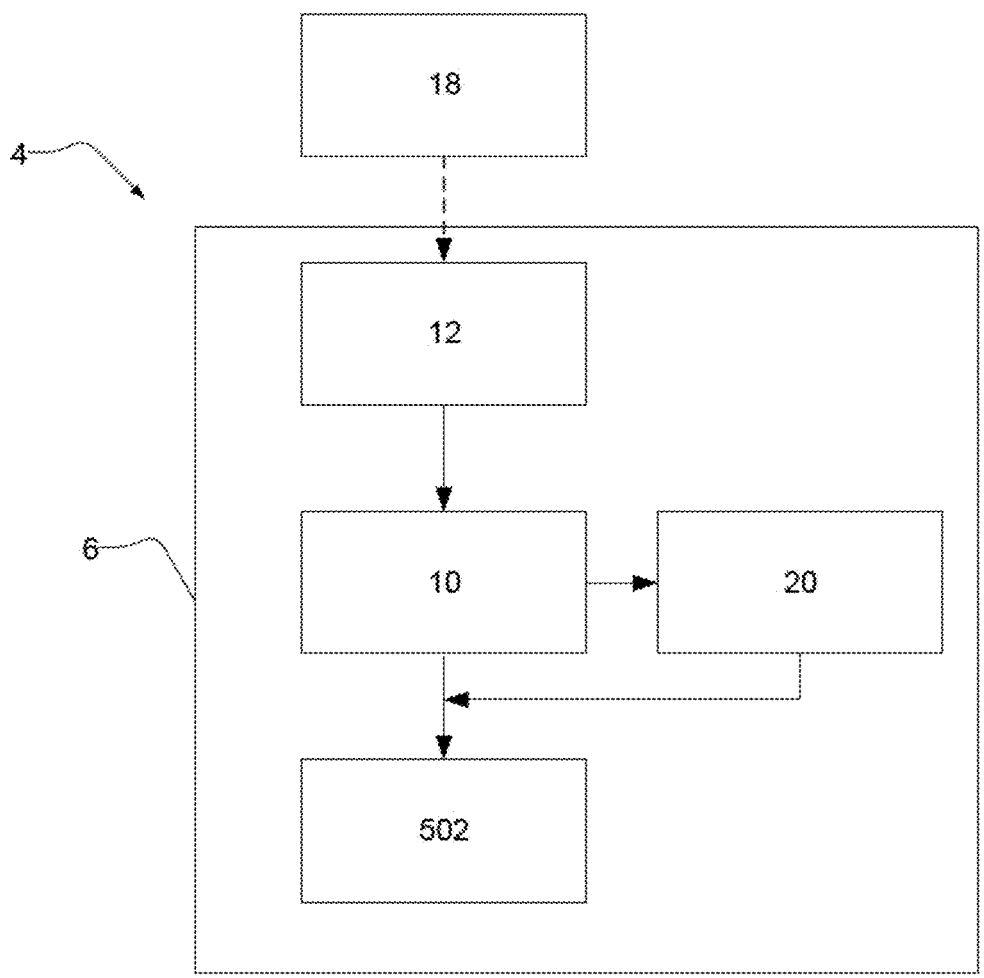
FIG. 10 schematically illustrates exemplary components of an exemplary auto injector.

FIG. 10 schematically illustrates exemplary components of an exemplary auto injector 4, such as the auto injector 4 as described in relation to previous figures. A second electrical connector 18 may be connected to a first electrical connector 12. By doing so a battery 10 of the auto injector may be charged. The battery 10 may supply electrical power to a motor 502. A processing unit 20 may be electrically powered by electrical power from the battery 10. The processing unit 20 may control the flow of electrical power to the motor 502. For example, the processing unit 20 may control the motor 502 to turn on or off. The processing unit 20, the motor 502, the battery 10 and the first electrical connector 12 is accommodated in the housing 6 of the auto injector 4.

The invention claimed is:

1. An auto injector for administering a medicament, the auto injector being connectable to an electrical power supply, the auto injector comprising:
   a housing accommodating a battery and a first electrical connector accessible via a connector opening in the housing and accepting a second electrical connector of the electrical power supply;
   a cartridge receiver configured to receive a cartridge containing the medicament;
   an ejector member movable along a longitudinal axis between a first ejector position and a second ejector position and being configured to follow movement of the cartridge along the longitudinal axis when the cartridge is received in the cartridge receiver;
   a blocking member coupled to the ejector member, the blocking member being configured to move between a blocking position wherein the connector opening is blocked and a non-blocking position wherein the connector opening is not blocked, wherein the blocking member is in the blocking position when the ejector member is in the second ejector position, and wherein the blocking member is in the non-blocking position when the ejector member is in the first ejector position; and
   an ejector lock configured to restrict movement of the ejector member along the longitudinal axis.

2. The auto injector according to claim 1, comprising a drive module coupled to actuate a plunger rod, the drive module being configured to receive electrical power from the battery.

3. The auto injector according to claim 1, wherein the ejector member has an ejector abutment face configured to abut a face of the cartridge.

4. The auto injector according to claim 1, comprising an ejector resilient member configured to exert a force on the ejector member.

5. The auto injector according to claim 1, wherein the blocking member comprises a first blocking coupling member and the ejector member comprises a second blocking coupling member, and wherein the first blocking coupling member and the second blocking coupling member are in engagement to translate movement of the ejector member to the blocking member.

6. The auto injector according to claim 1, wherein movement of the ejector member from a third ejector position to the second ejector position moves the blocking member from the non-blocking position to the blocking position, wherein the third ejector position is between the first ejector position and the second ejector position.

7. The auto injector according to claim 1, wherein movement of the ejector member from a fourth ejector position to the first ejector position moves the blocking member from the blocking position to the non-blocking position, wherein the fourth ejector position is between the first ejector position and the second ejector position.

8. The auto injector according to claim 1, wherein the ejector member and the blocking member are fixedly connected with respect to movement along the longitudinal axis.

9. The auto injector according to claim 1, wherein the ejector member is in the first ejector position when the cartridge is not received in the cartridge receiver, and wherein the ejector member is in the second ejector position when the cartridge is received in the cartridge receiver.

10. The auto injector according to claim 1, wherein the cartridge receiver is configured to receive the cartridge through a cartridge receiver opening in a cartridge receiving direction along the longitudinal axis.

11. The auto injector according to claim 1, wherein the blocking member is movable between the blocking position and the non-blocking position along the longitudinal axis.

12. The auto injector according to claim 1, wherein the blocking member is movable between the blocking position and the non-blocking position perpendicular to the longitudinal axis.

13. The auto injector according to claim 1, wherein the blocking member is prevented to move to the blocking position if the first electrical connector is coupled to the second electrical connector.

14. The auto injector according to claim 1, wherein the ejector member is prevented to move to the second ejector position if the blocking member is prevented to move to the blocking position.

15. A system comprising an auto injector according to claim 1, and a cartridge containing the medicament, wherein the cartridge is configured to be received in the cartridge receiver.

* * * * *